United States Patent [19]

Karami

[11] 4,047,529

[45] Sept. 13, 1977

[54] DISPOSABLE DIAPER WITH UNITARY TAPE FASTENER

[75] Inventor: Hamzeh Karami, Crystal Lake, Ill.

[73] Assignee: Colgate-Palmolive Company, New York, N.Y.

[21] Appl. No.: 715,783

[22] Filed: Aug. 19, 1976

[51] Int. Cl.² ............................................. A61F 13/16
[52] U.S. Cl. .................................... 128/287; 128/284; 128/290 R
[58] Field of Search ................... 128/284, 287, 290 R, 128/155, 156

[56] References Cited

U.S. PATENT DOCUMENTS

| 1,707,515 | 4/1929 | Evans | 161/147 X |
| 2,049,030 | 7/1936 | Strauss | 206/57 |
| 2,532,011 | 11/1950 | Dahlquist et al. | 161/406 X |
| 2,711,739 | 6/1955 | Fishbein | 128/335 |
| 2,755,800 | 7/1956 | Thompson | 128/156 |
| 2,940,884 | 6/1960 | White | 161/406 X |
| 3,315,677 | 4/1967 | Tyrrell, Jr. | 128/288 |
| 3,646,937 | 3/1972 | Gellert | 128/287 |
| 3,862,634 | 1/1975 | Small | 128/284 |
| 3,874,386 | 4/1975 | Kozak | 128/287 |
| 3,875,621 | 4/1975 | Karami | 24/73 VA |
| 3,920,019 | 11/1975 | Schaar | 128/287 |

*Primary Examiner*—Aldrich F. Medbery
*Attorney, Agent, or Firm*—Powell L. Sprunger

[57] ABSTRACT

A disposable diaper comprising, an absorbent pad assembly having opposed surfaces, and at least one side edge. The diaper has a tape fastener comprising a folded tape strip having opposed front and back surfaces, first and second sections, and a connecting section intermediate the first and second sections. The first section is attached to a surface of the pad assembly adjacent the side edge, and the second section has adhesive on a surface releasably attached to one of the first and connecting sections.

7 Claims, 14 Drawing Figures

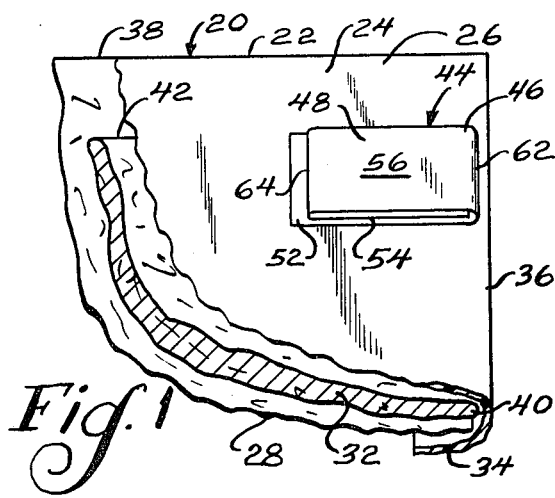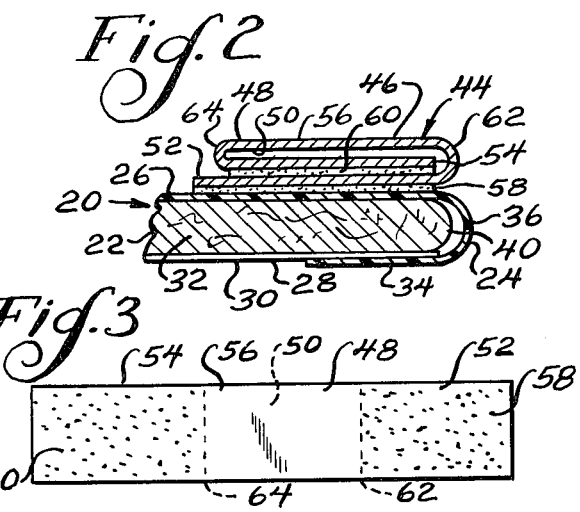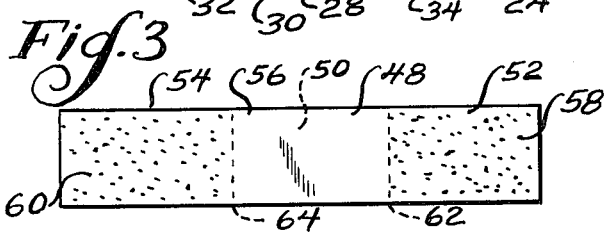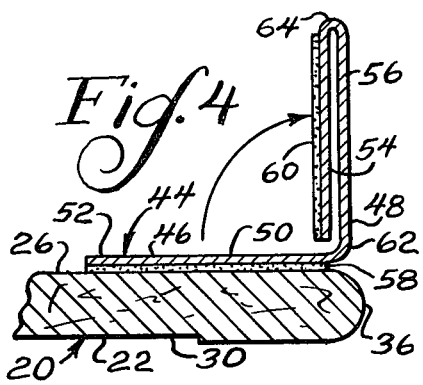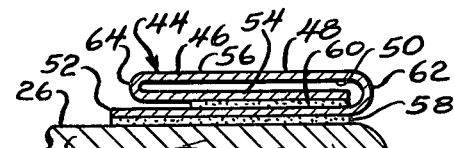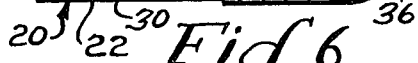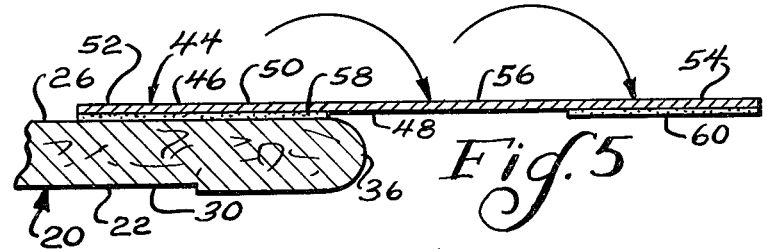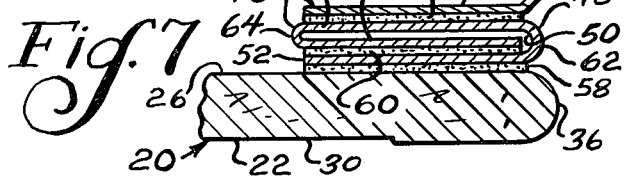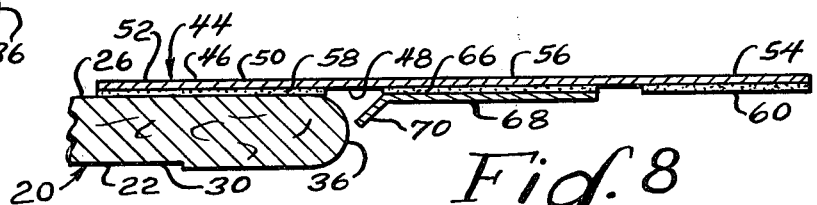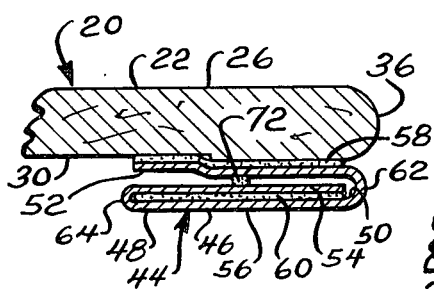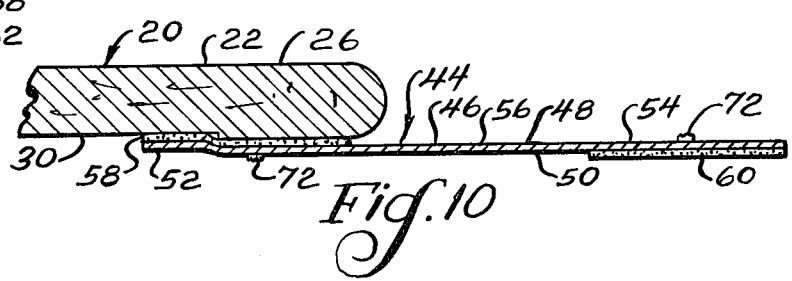

DISPOSABLE DIAPER WITH UNITARY TAPE FASTENER

BACKGROUND OF THE INVENTION

The present invention relates to absorbent articles, and more particularly to disposable diapers.

In the past, a various assortment of disposable diapers have been proposed for use on infants, and have become increasingly popular since they may be discarded after a single use and need not be laundered. Such diapers are generally constructed with a fluid impervious backing sheet, a fluid pervious cover or top sheet, and an absorbent pad located intermediate the backing and cover sheets.

Many of the diapers have been provided with tape fasteners which are used to secure the diaper about the infant. Such fasteners generally take the form of a pressure-sensitive tape strip having a first end attached to the diaper and a second securement end which is attached to another part of the diaper during placement. Prior to use, the adhesive on the securement end must be covered to prevent premature contact of the adhesive against the diaper or other article. Hence, in one form, the fasteners have been provided with separate release sheets which cover the adhesive on the securement ends. However, this form of tape fastener has been found lacking in that the release sheets must be discarded when removed at the time of diaper placement, thus causing inconvenience to the parents. In an alternative form, the separate release sheets have been anchored to the diaper itself, and the securement ends are peeled from the release sheets during placement of the diaper. However, an overriding consideration in construction of the diaper is the cost of manufacture, since the diaper must be inexpensive to the consumer due to its disposability. Thus, in either form, separate release sheets must be provided for the fastener which increases the cost of diaper materials and the complexity of manufacture, both of which add to the cost of the diaper.

SUMMARY OF THE INVENTION

A principal feature of the present invention is the provision of a disposable diaper having a tape fastener of simplified construction and reduced cost.

The diaper of the present invention comprises, an absorbent pad assembly having opposed surfaces, and at least one side edge. The diaper has a tape fastener comprising a folded tape strip having opposed front and back surfaces, first and second sections, and a connecting section intermediate the first and second sections. The first section has the front surface attached to a surface of the pad assembly adjacent the side edge, and the second section has adhesive on a surface being releasably attached to a surface of the first section or connecting section.

A feature of the present invention is that the tape fastener eliminates the necessity for a separate release to cover the adhesive on the second securement section.

Thus, a feature of the present invention is that the cost of materials for the tape fastener and diaper is reduced by elimination of the separate release sheet.

Another feature of the invention is that the tape strip may be unfolded for use during placement of the diaper in a simplified manner.

Still another feature of the present invention is that the tape fastener may be made in a simplified manner, thus reducing the cost of the diaper to the consumer.

Further features will become more fully apparent in the following description of the embodiments of this invention and from the appended claims.

DESCRIPTION OF THE DRAWINGS

In the drawings:

FIG. 1 is a fragmentary back plan view of a disposable diaper showing a tape fastener of the present invention;

FIG. 2 is a fragmentary sectional view of the diaper of FIG. 1;

FIG. 3 is a plan view of a tape strip used in the tape fastener of FIG. 1;

FIGS. 4 and 5 are fragmentary sectional views illustrating steps in unfolding the tape fastener during placement of the diaper.

FIG. 6 is a fragmentary sectional view of a diaper having another embodiment of the tape fastener of the present invention;

FIG. 7 is a fragmentary sectional view of a diaper having another embodiment of the tape fastener of the present invention;

FIG. 8 is a fragmentary sectional view of the diaper of FIG. 7 illustrating the fastener in an extended configuration during placement of the diaper;

FIG. 9 is a fragmentary sectional view of a diaper having another embodiment of the tape fastener of the present invention;

FIG. 10 is a fragmentary sectional view showing the fastener of FIG. 9 in an extended configuration during placement of the diaper;

DESCRIPTION OF THE PREFERRED EMBODIMENTS

Figure 11:
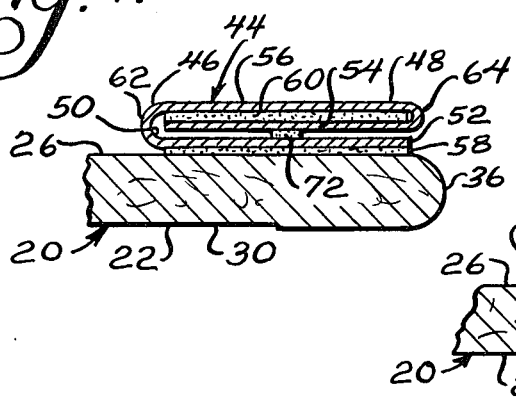
FIG. 11 is a fragmentary sectional view of a diaper having another embodiment of the tape fastener of the present invention.

Referring now to FIGS. 1 and 2, there is shown a disposable diaper generally designated 20 having an absorbent pad assembly 22. The pad assembly 22 has a fluid impervious backing sheet 24, such as polyethylene, defining a back surface 26 of the pad assembly 22, a fluid pervious cover or top sheet 28, such as a nonwoven material, defining a substantial portion of a front surface 30 of the pad assembly 22, and an absorbent pad 32 located intermediate the backing sheet 24 and cover sheet 28. The pad 32 may be made of any suitable material, such as comminuted wood pulp known in the art as fluff. As shown, the backing sheet 24 may have lateral side margins 34 folded over and secured to the front surface of the pad assembly and overlying side portions of the pad 32. The pad assembly 22 has side edges 36 and end edges 38 connecting the side edges 36. The pad 32 has side edges 40, and end edges 42 connecting the side edges 40. In a preferred form, the side edges 40 of the pad are located adjacent the side edges 36 of the pad assembly 22.

Referring now to FIGS. 1-3, the diaper 20 has a tape fastener generally designated 44 comprising a pressure-sensitive tape strip 46. As shown, the tape strip 46 has a front surface 48, an opposed back surface 50, a first end section 52, a second end section 54, and a connecting section 56 extending between and located intermediate the first section 52 and second end section 54. The first end section 52 has adhesive 58 on the front surface 48, while the second end section 54 has adhesive 60 on the front surface 48. The first end section 52 also has a release back surface 50 for a purpose which will be described below, and for convenience the entire back surface of the tape strip 46 may have release properties, if desired. Thus, the backing of the tape strip 46 may be made of a suitable paper material having a silicone release back surface, or may be made of a polymeric material, such as polyethylene, such that the adhesive 60 on the second end section 54 has a moderate affinity for the back surface 50 on the first end section 52.

As shown in FIGS. 1 and 2, the connecting section 56 is separated from the first end section 52 by a first fold line 62, while the connecting section 56 is separated from the second end section 54 by a second fold line 64. The back surface 50 of the second end section 54 is folded against the back surface 50 of the connecting section 56 about the second fold line 64, and the second end section 54 and connecting section 56 are folded about the first fold line 62 over the back surface 50 of the first end section 52. The adhesive 58 on the front surface of the first end section 52 is attached to the back surface 26 of the pad assembly 22 with the first fold line 62 located adjacent the side edge 36 of the pad assembly 22, while the adhesive 60 on the front surface of the second end section 54 is releasably attached to the back surface 50 of the first end section 52. Thus, the tape strip 46 is folded into a compact configuration on the back surface 26 of the pad assembly and in a position ready for use. As shown, the front surface 48 of the connecting section 56 is free of adhesive, and, if this surface has release properties, the entire folded tape structure may be wound into rolls with the adhesive on the front surface of the first end section 52 being releasably attached to the front surface 48 of the connecting section 56. Accordingly, the folded tape strip may be unwound from the rolls during manufacture and cut into lengths during attachment on the diaper to simplify the manufacturing procedure. Additionally, the tape fastener of the present invention eliminates the necessity for a separate release sheet to cover the outer securement end, such a release sheet need not be discarded during placement of the diaper and the cost of materials for the tape fastener and diaper has been reduced.

In use, as illustrated in FIG. 4, the second end section 54 and connecting section 56 may be pulled by the user in order to peel the adhesive 60 on the second end section 54 from the release back surface 50 of the first end section 52, after which the second end section 54 and connecting section 56 are unfolded about the first fold line 62 toward the side edge 36 of the pad assembly. Next, with reference to FIGS. 4 and 5, the second end section 54 is unfolded about the second fold line 64 until the connecting section 56 and second end section 54 extend outwardly from the side edge 36 of the pad assembly, as shown in FIG. 5. In this configuration, the adhesive 60 on the second end section 54 has been exposed and positioned for securement of the second end section 54 to another portion of the diaper during placement. Thus, the tape fastener of the present invention permits ready unfolding of the tape strip and positioning for securing the diaper about an infant during use.

Another embodiment of the present invention is illustrated in FIG. 6, in which like reference numerals designate like parts. In this embodiment, the adhesive 60 on the front surface 48 of the second end section 54 is spaced from the second fold line 64 in order to provide an adhesive free tab for convenient removal of the second end section 54 from the back surface 50 of the first end section 52. Thus, the user may grasp the second end section 54 and connecting section 56 adjacent the second fold line 64 in order to peel the adhesive 60 on the second end section 54 from the first end section 52.

Another embodiment of the tape fastener of the present invention is illustrated in FIGS. 7 and 8, in which like reference numerals designate like parts. In this embodiment, the connecting section 56 has adhesive 66 on the front surface 48 of the connecting section 56, and the adhesive 66 is covered by a release sheet 68 which is releasably attached to the adhesive 66. With reference to FIG. 8, during use, the tape fastener may be unfolded, and the adhesive 60 on the second end section 54 is utilized in a manner as previously described to secure the tape strip to another portion of the diaper during placement. However, in the event that it becomes necessary to remove the second end section 54 of the tape strip 46 from the diaper during use, e.g., in order to verify whether or not the diaper should be changed, the release sheet 68 may be peeled from the adhesive 66 on the connecting section 56 in order to expose fresh adhesive which may be used to reposition the tape fastener on the diaper for further use. Alternatively, the release sheet 68 may be removed after final use of the diaper, in order to expose fresh adhesive which may be used to secure the soiled diaper in a rolled or folded configuration for disposal. With reference to FIGS. 7 and 8, the release sheet 68 may have a free tab 70 at one end adjacent one of the fold lines, such as the fold line 62, in order to facilitate removal of the release sheet 68 from the adhesive 66 on the connecting section 56.

Figure 13:
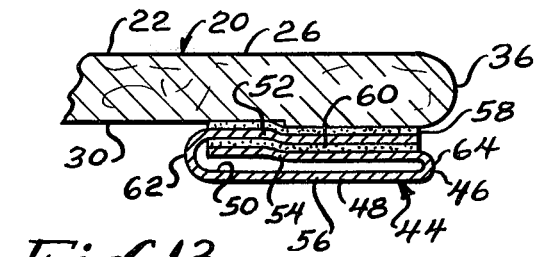
FIG. 13 is a fragmentary sectional view of a diaper having another embodiment of the tape fastener of the present invention.
Figure 14:
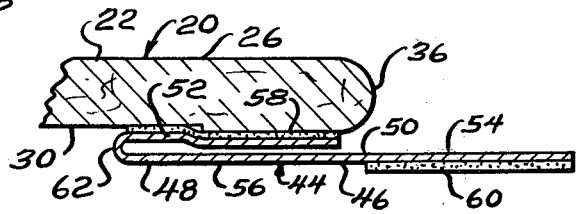
FIG. 14 is a fragmentary sectional view showing the tape fastener of FIG. 13 in an extended configuration during placement of the diaper.

Another embodiment of the present invention is illustrated in FIGS. 13 and 14, in which like reference numerals designate like parts. In this embodiment, the adhesive 58 on the first end section 52 is attached to the front surface 30 of the pad assembly 22, with the second fold line 64 between the connecting section 56 and the second end section 54 being positioned adjacent the side edge 36 of the pad assembly. As before, the adhesive 60 on the front surface of the second end section 54 is releasably attached to the back surface 50 of the first end section 52. During use, the adhesive 60 on the second end section 54 is peeled from the back surface 50 of the first end section 52, and the second end section 54 is unfolded about the second fold line 64. In this configuration, the connecting section 56 and second end section 54 extend outwardly from the first fold line 62, such that the adhesive 60 on the second end section 54 is exposed and positioned ready for attachment to a remote portion of the diaper during placement of the diaper about the infant.

Another embodiment of the tape fastener of the present invention is illustrated in FIGS. 9 and 10, in which like reference numerals designate like parts. In this embodiment, the adhesive 58 on the first end section 52 is attached to the front surface 30 of the pad assembly 22, with the first fold line 62 being located adjacent the side edge 36 of the pad assembly. The connecting section 56 has a release back surface 50, and the second end section 54 has adhesive on the back surface, such that the adhesive 60 on the back surface 50 of the second end section 54 is releasably attached to the back surface of the connecting section 56. As shown, the front surface 48 of the second end section 54 is attached by suitable means to the back surface 50 of the first end section 52, such as by a spot of adhesive 72, in order to maintain the tape strip 46 in a folded configuration. During use, the second end section 54 and connecting section 56 are pulled slightly in order to rupture or peel the spot of adhesive 72, after which the second end section 54 and connecting section 56 are unfolded about the first fold line 62. Next, with reference to FIG. 10, the second end section 54 is unfolded about the second fold line 64 while peeling the adhesive 60 of the second end section 54 from the back surface 50 of the connecting section 56. In this configuration, as shown, the connecting section 56 and second end section 54 extend past the side edge 36 of the pad assembly, with the adhesive 60 on the second end section 54 being exposed on the back surface 50 of the second end section 54 in a position for use while securing the diaper about the infant.

Figure 12:
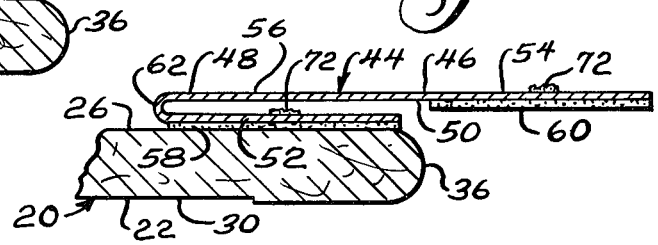
FIG. 12 is a fragmentary sectional view showing the tape fastener of FIG. 11 in an extended configuration during placement of the diaper.

Another embodiment of the present invention is illustrated in FIGS. 11 and 12, in which like reference numerals designate like parts. In this embodiment, the adhesive 58 on the first end section 52 is secured to the back surface 26 of the pad assembly 22, with the second fold line 64 being located adjacent the side edge 36 of the pad assembly 22. The second end section 54 has adhesive 60 on the back surface, and the connecting section 56 has a release back surface 50. The adhesive 60 on the second end section 54 is releasably attached to the back surface 50 of the first end section 52 by suitable means, such as by a spot of adhesive 72. During use, the second end section 54 and connecting section 56 are unfolded slightly about the first fold line 62 in order to rupture or peel the spot of adhesive 72 and free the second end section 54 from the back surface of the first end section 52. Next, the adhesive 60 on the second end section 54 is peeled from the back surface 50 of the connecting section 56, and the second end section 54 is unfolded about the second fold line 64, such that the second end section 54 extends outwardly from the side edge 36 of the pad assembly 22, as shown in FIG. 12. In this configuration, the adhesive 60 on the second end section 54 has been exposed for use to secure the diaper about the infant, with the connecting section 56 and second end section 54 extending from the first fold line 62 of the tape strip 46.

The foregoing detailed description is given for clearness of understanding only, and no unnecessary limitations should be understood therefrom, as modifications will be obvious to those skilled in the art. For example, the terms "fold lines" and "folds" are used herein for convenience in designating locations adjacent inner ends of the first and second sections and opposed ends of the connecting section, and it will be apparent that actual creases in the tape strip are not required to obtain the tape fastener of the present invention.

I claim:
1. A disposable diaper, comprising:
an absorbent pad assembly having opposed surfaces, and at least one side edge; and
a tape fastener comprising, a tape strip having opposed front and back surfaces, first and second sections and a connecting section intermediate the first and second sections, said connecting section extending between a first fold of the tape strip located adjacent an inner end of the first section and a second fold of the tape strip located adjacent an inner end of the second section, with the back surface of the second section being folded against the back surface of the connecting section about the second fold, and with the connecting and second sections being folded over the back surface of the first section about the first fold, said first section having a release back surface and the front surface attached to a surface of the pad assembly adjacent said side edge, said second section having adhesive on the front surface and being releasably attached to the back surface of the first section.

2. The diaper of claim 1 in which the first section is secured to a back surface of the pad assembly with the first fold located adjacent said side edge.

3. The diaper of claim 1 in which the first section is secured to a front surface of the pad assembly with the second fold located adjacent said side edge.

4. The diaper of claim 1 in which the connecting section is free of adhesive on the front surface thereof.

5. The diaper of claim 1 in which the connecting section has adhesive on at least a portion of the front surface, and including a release sheet releasably covering the adhesive on the connecting section.

6. The diaper of claim 5 in which said release sheet includes a tab adjacent one of said folds being free of attachment from the tape strip.

7. The diaper of claim 1 wherein said second section is free of adhesive adjacent said second fold to provide a tab of the second and connecting sections adjacent the second fold for peeling the second section from the first section.

* * * * *